US012558448B2

(12) United States Patent
Flynn

(10) Patent No.: US 12,558,448 B2
(45) Date of Patent: Feb. 24, 2026

(54) IMMOBILIZED pH INDICATOR FOR BIOLOGICAL INDICATOR GROWTH INDICATION

(71) Applicant: Solventum Intellectual Properties Company, Maplewood, MN (US)

(72) Inventor: Jeffrey M. Flynn, Osceola, WI (US)

(73) Assignee: Solventum Intellectual Properties Company, Maplewood, MN (US)

( * ) Notice: Subject to any disclaimer, the term of this patent is extended or adjusted under 35 U.S.C. 154(b) by 763 days.

(21) Appl. No.: 17/906,119

(22) PCT Filed: Feb. 22, 2021

(86) PCT No.: PCT/IB2021/051486
§ 371 (c)(1),
(2) Date: Sep. 12, 2022

(87) PCT Pub. No.: WO2021/186267
PCT Pub. Date: Sep. 23, 2021

(65) Prior Publication Data
US 2023/0110772 A1 Apr. 13, 2023

Related U.S. Application Data

(60) Provisional application No. 62/990,483, filed on Mar. 17, 2020.

(51) Int. Cl.
*A61L 2/28* (2006.01)
*C12Q 1/22* (2006.01)

(52) U.S. Cl.
CPC . *A61L 2/28* (2013.01); *C12Q 1/22* (2013.01)

(58) Field of Classification Search
None
See application file for complete search history.

(56) References Cited

U.S. PATENT DOCUMENTS

| | | | |
|---|---|---|---|
| 3,346,464 A | 10/1967 | Ernst | |
| 3,661,717 A | 5/1972 | Nelson | |
| 4,029,597 A | 6/1977 | Neisius et al. | |
| 5,223,401 A | 6/1993 | Foltz et al. | |
| 5,252,484 A | 10/1993 | Matner et al. | |
| 6,562,297 B1 | 5/2003 | Bonstein et al. | |
| 6,623,955 B2 | 9/2003 | Matner et al. | |
| 2012/0149094 A1* | 6/2012 | Smith | A61L 2/28 |
| | | | 435/288.7 |
| 2013/0210048 A1* | 8/2013 | Chandrapati | C12Q 1/04 |
| | | | 435/31 |
| 2013/0302849 A1 | 11/2013 | Smith et al. | |
| 2014/0349335 A1 | 11/2014 | Chandrapati et al. | |
| 2015/0337354 A1* | 11/2015 | Ahimou | G01N 21/6428 |
| | | | 435/31 |
| 2017/0253845 A1 | 9/2017 | Amin | |

FOREIGN PATENT DOCUMENTS

| | | |
|---|---|---|
| EP | 0371682 A2 | 5/1996 |
| EP | 1201255 A2 | 6/2008 |
| WO | 2010045433 A1 | 4/2010 |
| WO | 2011011189 A1 | 1/2011 |
| WO | 2012061212 A1 | 5/2012 |
| WO | 2012061226 A1 | 5/2012 |
| WO | 2014189716 A1 | 11/2014 |
| WO | 2016057520 A1 | 4/2016 |

OTHER PUBLICATIONS

International Search Report for PCT International Application No. PCT/IB2021/051486, mailed on May 21, 2021, 6 pages.

* cited by examiner

*Primary Examiner* — Lore R Jarrett

(57) ABSTRACT

A self-contained biological indicator is provided. The biological indicator includes a housing having at least one liquid-impermeable wall that forms an opening into a compartment. Disposed in the housing are a plurality of test microorganisms; an aqueous liquid medium disposed in an openable container; and a pH indicator dye substrate having a pH indicator dye bound thereto. The pH indicator is not disposed in or in liquid contact with the aqueous liquid medium. The biological indicator further comprises a nutrient composition that facilitates germination and/or outgrowth of the test microorganism, if viable; The nutrient composition can be disposed in the housing or is disposed in the openable container that is in selective fluid communication with the compartment.

14 Claims, No Drawings

IMMOBILIZED pH INDICATOR FOR BIOLOGICAL INDICATOR GROWTH INDICATION

CROSS REFERENCE TO RELATED APPLICATIONS

This application is a national stage filing under 35 U.S.C. 371 of PCT/IB2021/051486, filed Feb. 22, 2021, which claims the benefit of U.S. Application No. 62/990,483, filed Mar. 17, 2020, the disclosure of which is incorporated by reference in its/their entirety herein.

TECHNICAL FIELD

The present disclosure generally relates to sterilization indicators, and particularly, to biological sterilization indicators and methods of assessing the efficacy of a sterilization process.

BACKGROUND

In a variety of industries, such as the health care industry but also in other industrial applications, it can be necessary to monitor the effectiveness of processes used to sterilize equipment such as medical devices, instruments and other disposable and non-disposable articles. In these settings, sterilization is generally defined as the process of completely destroying all viable sources of biological activity, such as microorganisms, including structures such as viruses and spores. As a standard practice, hospitals include a sterility indicator with a batch of articles to assay the lethality of the sterilization process. Both biological and chemical sterility indicators have been used.

One standard type of biological sterility indicator includes a known quantity of test microorganisms, for example *Geobacillus stearothermophilus* (formerly *Bacillus stearothermophilus*) or *Bacillus atrophaeus* (formerly *Bacillus subtilis*) spores, which can be many times more resistant to particular sterilization processes than other contaminating organisms. After the indicator is exposed to the sterilization process, the sources of biological activity (e.g., spores) can be incubated in a nutrient medium to determine whether any of the sources survived the sterilization process, with source metabolism and/or growth indicating that the sterilization process was insufficient to destroy all of the sources of biological activity.

Available chemical sterility indicators can be read immediately at the end of the sterilization process. However, the results indicate only that a particular condition was present during the sterilization process, such as the presence of a particular chemical or a temperature, and potentially, that the condition was reached for a certain period of time. On the contrary, the response of sources of biological activity to all conditions actually present can be a more direct and reliable test for how effective a sterilization process is in achieving sterilization.

SUMMARY

The present disclosure generally relates to a self-contained biological indicator and methods of assessing the efficacy of a sterilization process. The self-contained biological indicator comprises a pH indicator dye substrate disposed therein, the pH indicator dye substrate having a pH indicator dye bound thereto. The method of the present disclosure is useful to detect a pH change as an indicator of survival of at least one test microorganism exposed to a sterilization process. Advantageously, the substrate-bound pH indicator dye of the articles and methods of the present disclosure permits the use of pH indicator dyes that might otherwise negatively affect the germination and/or growth of a test microorganism in the biological indicator if the dye was present in a solution with the test microorganism. Alternatively or additionally, the use of an immobilized pH indicator in the biological indicator can permit the use of higher (or lower) quantities of pH indicator dye than are typically used in a biological indicator. Even further advantageously, the use of a substrate-bound pH indicator dye permits the disposal of the pH indicator dye in the biological indicator in a dry form, thus providing stability (e.g., against hydrolysis) during storage for greater lengths of time. Moreover, when the pH indicator dye substrate-bound pH indicator dye is used in a method that includes detection of an enzyme-catalyzed product of a fluorogenic or chromogenic enzyme substrate, it provides for more-rapid detection of the product than was previously possible.

In one aspect, the present disclosure provides a self-contained biological indicator. The self-contained biological indicator can comprise a housing having at least one liquid-impermeable wall that forms an opening into a compartment; a plurality of test microorganisms disposed in the housing; an aqueous liquid medium disposed in an openable container that is disposed in the housing; a nutrient composition that facilitates germination and/or outgrowth of the test microorganism, if viable; and a pH indicator dye substrate disposed in the housing, the pH indicator dye substrate having a pH indicator dye bound thereto, wherein the pH indicator is not disposed in or in liquid contact with the aqueous liquid medium. The nutrient composition can be disposed in the housing or is disposed in the openable container.

In any of the above embodiments, the pH indicator dye substrate can be substantially water-free. In any of the above embodiments, the pH indicator dye can be substantially water-free. In any of the above embodiments, the pH indicator dye substrate can comprise a cationic polymer. In any of the above embodiments, the pH indicator dye can be selected from the group consisting of thymol blue, tropeolin OO, methyl yellow, methyl orange, bromophenol blue, bromocresol green, methyl red, bromothymol blue, phenol red, chlorophenol red, neutral red, naphtholphthalein, phenolphthalein, thymolphthalein, alizarin yellow, tropeolin O, nitramine, trinitrobenzoic acid, thymol blue, bromophenol blue, tetrabromphenol blue, bromocresol green, bromocresol purple, methyl red, bromothymol blue, Congo red, and cresol red. In any one of the above embodiments, the plurality of test microorganisms can be disposed on a carrier. In certain embodiments, the pH indicator dye substrate can be the carrier. In any of the above embodiments, the aqueous liquid medium can comprise the nutrient that facilitates germination and/or growth of the test microorganism. In any of the above embodiments, the self-contained biological indicator further can comprise a fluorogenic or chromogenic enzyme substrate disposed in the housing.

In another aspect, the present disclosure provides a method assessing the efficacy of a sterilization process. The method can comprise positioning a biological indicator in a sterilization chamber, wherein the self-contained biological indicator comprises: a housing having at least one liquid-impermeable wall that forms an opening into a compartment, a plurality of test microorganisms disposed in the compartment, and a substantially water-free pH indicator dye substrate disposed in the compartment, the pH indicator dye substrate having a substantially water-free pH indicator dye bound thereto. The pH indicator dye is present on the pH indicator dye substrate substantially in a first state and the pH indicator dye can be converted to a second state that is optically distinguishable from the first state. The method further can comprise exposing the biological indicator in the sterilization chamber to the sterilization process; after the exposing the biological indicator in the sterilization chamber to the sterilization process, contacting in the housing of the biological indicator the test microorganisms and the pH indicator dye substrate with an aqueous liquid medium and a nutrient that facilitates germination and/or growth of the test microorganism; incubating the biological indicator for a period of time; and after incubating the biological indicator for the period of time, observing the pH indicator dye to detect the second state, wherein detecting a presence of the second state of the pH indicator dye on the pH indicator dye substrate indicates a lack of efficacy of the sterilization process and wherein detecting an absence of the second state of the pH indicator dye on the pH indicator dye substrate indicates efficacy of the sterilization process.

All scientific and technical terms used herein have meanings commonly used in the art unless otherwise specified. The definitions provided herein are to facilitate understanding of certain terms used frequently in this application and are not meant to exclude a reasonable interpretation of those terms in the context of the present disclosure. Unless otherwise indicated, all numbers in the description and the claims expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises", and variations thereof do not have a limiting meaning where these terms appear in the description and claims.

As used herein, "a," "an," "the," "at least one," and "one or more" are used interchangeably. Thus, for example, a substrate can be interpreted to mean "one or more" substrates.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to a self-contained sterilization indicator, and particularly, to a self-contained biological sterilization indicator. A self-contained biological indicator comprises all of the components necessary to assess the survival of a test microorganism contained therein and can be used to determine the lethality of a sterilizing process. The present disclosure generally relates to the construction of the biological sterilization indicator that allows for one or more of at least the following: providing a pH indicator dye bound (e.g., with high affinity) to a pH indicator dye substrate; housing a liquid (e.g., an aqueous liquid medium) separate from the pH indicator dye and one or more test microorganisms during sterilization and allowing for combination of the liquid and the test microorganisms with the pH indicator dye (i.e., bound to the pH indicator dye substrate) after sterilization; facilitating sterilant movement to a location (e.g., a closed end) of the biological sterilization indicator where one or more sources of test microorganisms are housed; holding an openable container (e.g., a frangible ampoule, such as a glass ampoule) that contains the liquid in a location isolated from the test microorganisms in the biological sterilization indicator during sterilization; releasing the liquid from the openable container during activation of the biological sterilization indicator (e.g., by fracturing the container); providing a substantially constant sterilant path; and generally controlling and/or facilitating fluid flow within the biological sterilization indicator (e.g., by employing one or more internal vents).

Pressurized steam or other common sterilants can be used to sterilize equipment and supplies used in healthcare environments. Small, self-contained indicators, such as biological sterilization indicators, can be used to verify the efficacy of the sterilization processes. These indicators can be biological and can contain sources of biological activity (e.g., test microorganisms).

Housing

For non-limiting examples of housings suitable for use in self-contained biological indicators, please see U.S. Pat. Nos. 3,661,717; 5,223,401 and 6,623,955; and U.S. Patent Application Publication Nos. 2013/0302849 and 2014/0349335; each of which is incorporated herein by reference in its entirety. In general, the housing refers to a container, usually an outer container, having at least one wall impermeable to a sterilant. The at least one wall forms a reservoir in which other components of the biological indicator are located. The housing may be disposed inside a process challenge device or may be a process challenge device itself. In some embodiments, the housing may have dimensions useful to produce a flat or generally planar biological indicator. This disclosure encompasses housings of any shape and dimensions.

The housing contains at least one opening that allows flow of a sterilant into the interior of the housing (sterilant pathway). In some embodiments, the housing may comprise a body with an opening and a cap to close that opening. In some embodiments, the cap may be capable of completely sealing the housing and eliminating any fluid communication between the interior of the housing and ambiance (e.g., closing the sterilant pathway). In general, the cap has an open position in which there is an opening (e.g., a gap) between the cap and the body of the container that allows flow of liquid or gas (e.g., a sterilant) into and out of the interior of the housing. The cap also has a closed position where the opening is sealed and any fluid flow through the gap is eliminated. In other embodiments, the cap may comprise vents that allow passage of a sterilant to the interior of the housing and create an additional sterilant pathway, even if the cap is present and in the closed position. In other preferred embodiments, however, when the cap comprises vents, placing the cap in the closed position simultaneously closes: (a) the gap between the cap and the body of the container and (b) the vents present on the cap, essentially closing the sterilant pathway.

In other embodiments, the cap may lack vents and the only sterilant pathway may be through the space between the cap and the body of the housing (or through another opening or vent, if present on the body) when the cap is the open position. In some embodiments, if vents exist on the housing, they are located on the cap. In embodiments where no other opening exists besides the opening between the cap and the body of the housing, then placing the cap in the closed position completely seals off the interior of the housing, which stops the fluid communication between the interior of the housing and ambience. In those embodiments, the sterilant pathway may be sealed when the cap is in the closed position.

pH Indicator Dye Substrate

A self-contained biological indicator of the present disclosure includes a pH indicator dye substrate disposed therein (e.g., disposed in the interior of the housing). The pH indicator dye substrate has a pH indicator dye bound thereto. The pH indicator dye can be bound to the pH indicator dye substrate by any means including, but not limited to covalent binding, ionic binding, hydrophobic interaction, and a combination of any two or more of the foregoing bonding means.

Preferably, the pH indicator dye is bound to the pH indicator dye substrate with high affinity (i.e., after 10 mg of the indicator dye-bound substrate is rinsed with deionized water and subsequently placed into 1 mL of deionized water; less than 10%, preferably less than 5%, and more preferably less than 1% of the indicator dye is released into the deionized water within 1 hour at 23 degrees C.).

In some embodiments, the pH indicator dye substrate can be formed of a variety of materials, provided that it binds the pH indicator dye with high affinity. The pH indicator dye substrate materials and/or its surface may be modified, if necessary, to bind the pH indicator dye. Examples of pH indicator dye substrate materials include, but are not limited to, cotton, glass wool, cloth, nonwoven polypropylene, nonwoven rayon, nonwoven polypropylene/rayon blend, nonwoven nylon, nonwoven glass fiber or other nonwoven fibers, filter papers, microporous hydrophobic and hydrophilic films, glass fibers, open celled polymeric foams, and semi-permeable plastic films (e.g., particle filled films, thermally induced phase separation (TIPS) membranes, etc.), and combinations thereof.

An example of a suitable pH indicator dye substrate material is a charged material (e.g., an anionically-charged material that binds (e.g., with high affinity) a pH indicator dye that is cationically charged in a solvent having a neutral pH (e.g., a pH about 6.5 to about 7.5). Alternatively, a suitable pH indicator dye substrate material is a cationically-charged material that binds (e.g., with high affinity) a pH indicator dye that is anionically charged in a solvent having a neutral pH (e.g., a pH about 6.5 to about 7.5). In certain embodiments, wherein the pH indicator dye substrate material comprises a cationic polymer, the cationic polymer is selected from the group consisting of a polyamide polymer, a polyethyleneimine polymer, a polyvinylidene difluoride polymer, and combinations of any two or more of the foregoing cationic polymers.

For example, in embodiments in which the pH indicator dye substrate can be used to bind bromocresol purple (BCP), the substrate can be formed of a charged nylon (such as a reprobing, charged transfer membrane available from GE Water & Process Technologies, Trevose, Pa., under the trade designation "MAGNAPROBE" (e.g., 0.45 micron pore size, 30 cm×3 m roll, Catalog No. NP0HY00010, Material No. 1226566)). In certain embodiments, the pH indicator dye substrate material can be a hydrophobic material that binds the pH indicator dye with high affinity through hydrophobic interaction, for example. Other suitable combinations of pH indicator dye substrate material and pH indicator dyes would be apparent to a person having ordinary skill in the art.

In some embodiments, it is contemplated that a particular pH indicator dye substrate material can be treated (e.g., by exposure to a plasma, a corona treatment, or an e-beam process to create surface charges on the substrate material) to facilitate binding of the pH indicator dye to the pH indicator dye substrate. Alternatively, or additionally, binding of the pH indicator dye to the pH indicator dye substrate may be done in a solvent having a non-neutral pH in order to facilitate the ionic conditions that favor binding of the dye to the substrate.

In any embodiment, the pH indicator dye substrate can be substantially water-free. In any embodiment, the pH indicator dye bound to the pH indicator dye substrate can be substantially water-free. "Substantially water-free", as used herein refers to a substrate or a pH indicator dye that, after excess water has been removed by drying, has a water content no greater than about the water content of the dehydrated substrate or dye once it has been permitted to equilibrate with the ambient environment.

The pH indicator dye substrate is shaped and dimensioned to fit inside the housing of the biological indicator in a location where it can be brought into contact (e.g., when the biological indicator is activated) with an aqueous medium that is in fluid contact with test microorganisms and a nutrient for growing the test microorganisms, each as disclosed herein. In certain embodiments, the pH indicator dye substrate may be substantially planar (e.g., as a membrane filter). In some embodiments, the pH indicator dye substrate may be shaped and dimensioned (relative to the other components in the biological indicator) similar to the filter paper 16 in U.S. Pat. No. 3,661,717; the carrier 46 or wick strip 76 of U.S. Pat. No. 5,223,401; or the substrate 119 of U.S. Patent Application Publication No. 2013/03022849, for example. In some embodiments, the pH indicator dye substrate may be fibrous (e.g., as a yarn). In some embodiments, the pH indicator dye substrate may be particulate (e.g., as a porous or a nonporous bead).

Test Microorganisms (e.g., Spores)

Generally, test microorganisms chosen to be used in a biological indicator are particularly resistant to a given sterilization process. In certain embodiments, the biological indicators of the present disclosure include a viable culture of a known species of microorganism, usually in the form of microbial spores. Spores (e.g., bacterial spores), rather than the vegetative form of the microorganisms, are used at least partly because vegetative microorganisms are known to be relatively easily killed by sterilizing processes. Conversely, spores are relatively more resistant to sterilizing processes. Additionally, spores also have superior storage characteristics and can remain in their dormant state for years. As a result, sterilization of an inoculum of a standardized spore strain provides a higher degree of confidence that inactivation of all microorganisms in a sterilizing chamber has occurred.

A self-contained biological indicator of the present disclosure includes a plurality of test microorganisms disposed therein (e.g., disposed in the interior of the housing). The test microorganisms may be of one or more species. Typically, the biological indicator contains at least $10^3$, at least $10^4$, at least $10^5$, at least $10^6$, at least $10^7$, or at least $10^8$ test microorganisms By way of example only, the present disclosure describes the microorganisms used in the biological indicator as being "spores;" however, it should be understood that the type of microorganism (e.g., spore) used in a particular embodiment of the biological indicator is selected for being resistant to the particular sterilization process contemplated (more resistant than the microorganisms normally present on the items to be sterilized so that inactivation of the test microorganisms indicates a successful sterilization). Accordingly, different embodiments of the present disclosure using different sterilants may use different microorganisms, depending on the sterilization process for which the particular embodiment is intended.

In general, the test microorganisms used in a particular system are selected according to the sterilization process at hand. For example, for a steam sterilization process, *Geobacillus stearothermophilus* or *Bacillus stearothermophilus* spores can be used. In another example, for an ethylene oxide sterilization process, *Bacillus atrophaeus* (formerly *Bacillus subtilis*) spores can be used. In some embodiments, the spores can include, but are not limited to, at least one of *Geobacillus stearothermophilus, Bacillus stearothermophilus, Bacillus subtilis, Bacillus atrophaeus, Bacillus megate-*

*rium, Bacillus coagulans, Clostridium sporogenes, Bacillus pumilus*, or combinations thereof.

Aqueous Liquid Medium

The aqueous liquid medium is disposed in an openable container disposed in the interior of the housing formed by the at least one wall of the housing. In certain embodiments, the solvent of the aqueous liquid medium is water. In certain embodiments, the aqueous liquid medium may have dissolved and/or suspended therein a nutrient composition (described hereinbelow) that facilitates germination and/or outgrowth of a viable test microorganism. In certain embodiments, the aqueous liquid medium may have dissolved and/or suspended therein one or more enzyme substrate as disclosed herein. In certain embodiments, the aqueous liquid medium may have dissolved and/or suspended therein a salt, including, but not limited to, sodium chloride, potassium chloride, calcium chloride, or the like, or a combination thereof. In certain embodiments, the salt may comprise a buffer (e.g., sodium phosphate, potassium phosphate) for buffering the aqueous liquid medium at a pH suitable for germination and/or growth of the test microorganisms. In certain embodiments, the aqueous liquid medium may have dissolved and/or suspended therein a component selected from the group consisting of a nutrient composition as disclosed herein, an enzyme substrate as disclosed herein, a salt as disclosed herein, a buffer as disclosed herein, and a combination of any two or more of the foregoing components.

Nutrient Composition

A self-contained biological indicator of the present disclosure comprises a nutrient composition that facilitates germination and/or outgrowth of one of the plurality of test microorganisms, if viable. Suitable nutrients for the nutrient composition may be provided initially in a dry form (e.g., powdered form, tablet form, caplet form, capsule form, a film or coating, entrapped in a bead or other carrier, another suitable shape or configuration, or a combination thereof) disposed in the interior of the biological indicator. Alternatively or additionally a suitable nutrient may be disposed in the aqueous liquid medium.

The nutrient composition can include, for example, one or more sugars, including, but not limited to, glucose, fructose, dextrose, maltose, trehalose, cellobiose, or the like, or a combination thereof. Alternatively or additionally, the nutrient composition may include complex media, such as peptone, tryptone, phytone peptone, yeast extract, soybean casein digest, other extracts, hydrolysates, etc., or a combination thereof. In other embodiments, the nutrient composition may comprise a combination of one or more complex media components and other specific nutrients. In some embodiments, the nutrient composition can further include at least one amino acid, including, but not limited to, at least one of methionine, phenylalanine, alanine, tyrosine, and tryptophan.

As part of a self-contained biological indicator, the aqueous liquid medium is typically present in or with the biological indicator throughout the sterilization procedure but is isolated from (e.g., in the openable container) the test microorganisms until desired. Other components (e.g., the nutrient and/or the enzyme substrate and/or other components (e.g., a neutralizer, a buffer component, a salt) in the biological indicator may also be present in or with the biological indicator throughout the sterilization procedure but isolated from (e.g., in the openable container) the test microorganisms until desired. After the sterilization process is completed and the biological indicator is used to determine the efficacy of the sterilization, the aqueous liquid medium is placed in contact with the test microorganisms resulting in a mixture. In this disclosure, placing the aqueous liquid medium with the test microorganisms includes activating the openable container so that the aqueous liquid medium is released and contacts the test microorganisms. This process may include mixing of the aqueous liquid medium with the spores, such as manual or mechanical shaking of the housing of the biological indicator so that the aqueous liquid medium adequately mixes with the test microorganisms, the nutrient, and the other components, if present.

Enzymes and Enzyme Substrates

A self-contained biological indicator of the present disclosure optionally comprises an enzyme capable of catalyzing the cleavage of an enzyme substrate to produce a fluorescently detectable compound. In certain embodiments, the enzyme can be present in and/or on the test microorganisms, or the test microorganisms are capable of producing such an enzyme, or both. The enzymes useful in biological indicators of the present disclosure include extracellular and intracellular enzymes whose activity correlates with the viability of at least one of the microorganisms commonly used to monitor sterilization efficacy ("test" microorganism or "test spores"). In this context, "correlates" means that the enzyme activity, over background, can be used to demonstrate survival of at least one of the test microorganisms. The enzyme should be one which, following a sterilization cycle which is sublethal to the test microorganism, remains sufficiently active to react with an enzyme substrate for the enzyme, within twenty-four hours, and in preferred embodiment within one hours or less, yet be inactivated or appreciably reduced in activity following a sterilization cycle which would be lethal to the test microorganism.

Examples of suitable enzymes include α-glucosidase, α-galactosidase, lipase, esterase, acid phosphatase, alkaline phosphatase, proteases, aminopeptidase, β-glucosidase, β-galactosidase, α-glucoronidase, β-glucoronidase, phosphohydrolase, α-mannosidase, β-mannosidase, α-L-fucosidase, leucine aminopeptidase, α-L-arabinofuranoside, cysteine aminopeptidase, valine aminopeptidase, xylosidase, α-L-iduronidase, glucanase, cellobiosidase, cellulase, α-arabinosidase, glycanase, sulfatase, butyrate, glycosidase, arabinoside, and a combination of any two or more of the foregoing enzymes.

In the context of this application, an enzyme substrate comprises a substance or mixture of substances that, when acted upon by an enzyme, are converted into an enzyme-modified product. Although the preferred enzyme substrate produces a fluorescently detectable compound, in other embodiments, the product of the enzymatic action may be a luminescent or colored material. In other embodiments, however, the enzyme substrate can consist of a compound which when reacted with the enzyme, will yield a product that will react with an additional compound or composition to yield a luminescent, fluorescent, or colored material. Preferably, if the enzyme substrate is to be included in the indicator device during sterilization, the enzyme substrate should not spontaneously break down or convert to a detectable product during sterilization or incubation. For example, in devices used to monitor steam and dry heat sterilization, the enzyme substrate must be stable at temperatures between about 20° C. and 180° C. Preferably also, where the enzyme substrate is to be included with conventional growth media, it must be stable in the growth media, e.g., not auto fluoresce in the growth media. Advantageously, whether the enzyme substrate is fluorogenic or chromogenic, having the pH indicator bound (e.g., with high affinity) to the pH indicator dye substrate makes it significantly less likely the pH indicator dye will interfere with detection in the aqueous liquid medium of the product of the enzyme reaction.

In general, there are two basic types of enzyme substrate that can be used in the biological indicators of this disclosure. The first type of enzyme substrate can be either fluorogenic (or chromogenic), and can be given a chemical formula such as, AB. When acted upon by the enzyme, AB breaks down into the products A and B. B, for example, could be either fluorescent or colored. A specific example of a fluorogenic enzyme substrate of this type are salts comprising a 4-methylumbelliferyl component. Other fluorogenic enzyme substrates of this type include the derivatives of 7-amido-4-methylcoumarin (7-AMC), indoxyl and fluorescein. An example of a chromogenic enzyme substrate of this type is 5-bromo-4-chloro-3-indolyl phosphate. In the presence of phosphatase, the enzyme substrate will be broken down to form indigo blue and phosphate. Other chromogenic enzyme substrates of this type include derivatives of 5-bromo-4-chloro-3-indolyl, nitrophenol and phenolphthalein, listed below.

The second type of enzyme substrate can be given the chemical formula CD, for example, which will be converted by a specific enzyme into C and D. In this case, however, neither C nor D will be fluorescent or colored, but either C or D is capable of being further reacted with compound Z to give a fluorescent or colored compound, thus indicating enzyme activity. A specific fluorogenic example of this type is the amino acid lysine. In the presence of the enzyme lysine decarboxylase, lysine loses a molecule of $CO_2$. The product resulting from the enzymatic decarboxylation of lysine is cadaverine, which is strongly basic. A basic indicator such as 4-methylumbelliferone can be incorporated and will fluoresce in the presence of a strong base. A chromogenic enzyme substrate of this type would be 2-naphthyl phosphate. The enzyme phosphatase reacts with the enzyme substrate to yield beta-naphthol. The liberated beta-naphthol reacts with a chromogenic reagent containing 1-diazo-4-benzoylamino-2,5-diethoxybenzene, commercially available as "Fast Blue BB Salt" from Sigma Chemical, to produce a violet color.

As mentioned above, a preferred enzyme substrate in some embodiments is a fluorogenic enzyme substrate, defined herein as a compound capable of being enzymatically modified, e.g., by hydrolysis or other enzymatic action, to give a derivative fluorophore that has a measurably modified or increased fluorescence.

A person having ordinary skill in the art would understand that suitable fluorogenic compounds are in themselves either non-fluorescent or meta-fluorescent (i.e., fluorescent in a distinctly different way e.g., either by color or intensity, compared to the corresponding enzyme-modified products). In that regard, appropriate wavelengths of excitation and detection, in a manner known to users of fluorometric techniques, are used to separate the fluorescence signal developed by the enzyme modification from any other fluorescence that may be present.

Non-limiting examples of suitable enzymatic substrates can include, for example, derivatives of coumarin including 7-hydroxycoumarin (also known as umbelliferone or 7-hydroxy-2H-chromen-2-one) derivatives and 4-methylumbelliferone (7-hydroxy-4-methylcoumarin) derivatives including: 4-methylumbelliferyl alpha-D-glucopyranoside, 4-methylumbelliferyl alpha-D-galactopyranoside, 4-methylumbelliferyl heptanoate, 4-methylumbelliferyl palmitate, 4-methylumbelliferyl oleate, 4-methylumbelliferyl acetate, 4-methylumbelliferylnonanoate, 4-methylumbelliferyl caprylate, 4-methylumbelliferyl butyrate, 4-methylumbelliferyl-beta-D-cellobioside, 4-methylumbelliferyl acetate, 4-methylumbelliferyl phosphate, 4-methylumbelliferyl sulfate, 4-methylumbelliferyl-beta-trimethylammonium cinnamate chloride, 4-methylumbelliferyl-beta-D-N,N',N''-triacetylchitotriose, 4-methylumbelliferyl-beta-D-xyloside, 4-methylumbelliferyl-N-acetyl-beta-D-glucosaminide, 4-methylumbelliferyl-N-acetyl-alpha-D-glucosaminide, 4-methylumbelliferyl propionate, 4-methylumbelliferyl stearate, 4-methylumbelliferyl-alpha-L-arabinofuranoside, 4-methylumbelliferyl alpha-L-arabinoside; 4-methylumbelliferyl-beta-D-N,N'-diacetyl chitobioside, 4-methylumbelliferyl elaidate, 4-Methylumbelliferyl-alpha-D-mannopyranoside, 4-methylumbelliferyl-beta-D-mannopyranoside, 4-methylumbelliferyl-beta-D-fucoside, 4-methylumbelliferyl-alpha-L-fucoside, 4-methylumbelliferyl-beta-L-fucoside, 4-methylumbelliferyl-alpha-D-galactoside, 4-methylumbelliferyl-beta-D-galactoside, 4-trifluoromethylumbelliferyl beta-D-galactoside, 4-methylumbelliferyl-alpha-D-glucoside, 4-methylumbelliferyl-beta-D-glucoside, 4-methylumbelliferyl-7,6-sulfo-2-acetamido-2-deoxy-beta-D-glucoside, 4-methylumbelliferyl-beta-D-glucuronide, 6,8-difluor-4-methylumbelliferyl-beta-D-glucuronide, 6,8-difluoro-4-methylumbelliferyl-beta-D-galactoside, 6,8-difluoro-4-methylumbelliferyl phosphate, 6,8-difluoro-4-methylumbelliferyl beta-D-xylobioside, for example. The second enzyme substrate can also be derivatives of 7-amido-4-methylcoumarin, including Ala-Ala-Phe-7-amido-4-methylcoumarin, Boc-Gln-Ala-Arg-7-amido-4-methylcoumarin hydrochloride, Boc-Leu-Ser-Thr-Arg-7-amido-4-methylcoumarin, Boc-Val-Pro-Arg-7-amido-4-methylcoumarin hydrochloride, D-Ala-Leu-Lys-7-amido-4-methylcoumarin, L-Alanine 7-amido-4-methylcoumarin trifluoroacetate salt, L-Methionine 7-amido-4-methylcoumarin trifluoroacetate salt, L-Tyrosine 7-amido-4-methylcoumarin, Lys-Ala-7-amido-4-methylcoumarin dihydrochloride, N-p-Tosyl-Gly-Pro-Arg 7-amido-4-methylcoumarin hydrochloride, N-Succinyl-Ala-Ala-Phe-7-amido-4-methylcoumarin, N-Succinyl-Ala-Ala-Pro-Phe-7-amido-4-methylcoumarin, N-Succinyl-Ala-Phe-Lys 7-amido-4-methylcoumarin acetate salt, N-Succinyl-Leu-Leu-Val-Tyr-7-Amido-4-methylcoumarin, D-Val-Leu-Lys 7-amido-4-methylcoumarin, Fmoc-L-glutamic acid 1-(7-amido-4-methylcoumarin), Gly-Pro-7-amido-4-methylcoumarin hydrobromide, L-Leucine-7-amido-4-methylcoumarin hydrochloride, L-Proline-7-amido-4-methylcoumarin hydrobromide; other 7-hydroxycoumarin derivatives including 3-cyano-7-hydroxycoumarin (3-cyanoumbelliferone), and 7-hydroxycoumarin-3-carboxylic acid esters such as ethyl-7-hydroxycoumarin-3-carboxylate, methyl-7-hydroxycoumarin-3-carboxylate, 3-cyano-4-methylumbelliferone, 3-(4-imidazolyl)umbelliferone; derivatives of fluorescein including 2',7'-Bis-(2-carboxyethyl)-5-(and-6-)carboxyfluorescein, 2',7'-bis-(2-carboxypropyl)-5-(and-6-)-carboxyfluorescein, 5- (and 6)-carboxynaphthofluorescein, Anthofluorescein, 2',7'-Dichlorofluorescein diacetate, 5(6)-Carboxyfluorescein, 5(6)-Carboxyfluorescein diacetate, 5-(Bromomethyl)fluorescein, 5-(Iodoacetamido)fluorescein, 5-([4,6-Dichlorotriazin-2-yl]amino)fluorescein hydrochloride, 6-Carboxyfluorescein, Eosin Y, Fluorescein diacetate 5-maleimide, Fluorescein-O'-acetic acid, O'-(Carboxymethyl)fluoresceinamide, anthofluorescein, rhodols, halogenated fluorescein; derivatives of rhodamine including: Tetramethylrhodamine, Carboxy tetramethyl-rhodamine, Carboxy-X-rhodamine, Sulforhodamine 101 and Rhodamine B; afluorescamine derivatives; derivatives of benzoxanthene dyes including: seminaphthofluorones, carboxy-seminaphthofluorones seminaphthofluoresceins, seminaphthorhodafluors; derivatives of cyanine including sulfonated pentamethine and septamethine cyanine.

In some embodiments, the enzyme whose activity is to be detected may be chosen from alpha-D-glucosidase, chymotrypsin, or fatty acid esterase. In the case of *Bacillus stearothermophilus*, the fluorogenic enzyme substrate is preferably 4-methylumbelliferyl-alpha-D-glucoside, 7-glutarylphenylalanine-7-amido-4-methyl coumarin, or 4-methylumbelliferyl heptanoate. If the enzyme whose activity is to be detected is alpha-L-arabinofuranosidase, e.g., derived from *Bacillus atrophaeus*, a preferred fluorogenic enzyme substrate is 4-methylumbelliferyl-alpha-L-arabinofuranoside. In preferred embodiments, 4-methylumbelliferyl alpha-D-glucopyranoside is the enzyme substrate used to produce the metabolic activity and the enzyme is a glucosidase, such as beta-D-glucosidase.

The concentration of enzyme substrate present in the aqueous liquid medium depends upon the identity of the particular enzyme substrate and enzyme, the amount of enzyme-product that must be generated to be detectable, either visually or by instrument, and the amount of time that one is willing to wait in order to determine whether active enzyme is present in the reaction mixture. Preferably, the amount of enzyme substrate is sufficient to react with any residual active enzyme present, after the sterilization cycle, within about an eight-hour period of time, such that at least $10^{-8}$ molar enzyme-modified product is produced. In cases where the enzyme substrate is a 4-methylumbelliferyl derivative, the inventors have been found that its concentration in the aqueous liquid medium disclosed herein is preferably between about $10^{-5}$ and $10^{-3}$ molar. In some embodiments, the 4-methylumbelliferyl-$\alpha$-D-glucoside can be used, for example, at a concentration of about 0.05 to about 0.5 g/L (e.g., about 0.05 g/L, about 0.06 g/L, about 0.07 g/L, about 0.08 g/L, about 0.09 g/L, about 0.1 g/L, about 0.15 g/L, about 0.2 g/L, about 0.25 g/L, about 0.3 g/L, about 0.35 g/L, about 0.4 g/L, about 0.45 g/L, about 0.5 g/L) in the aqueous mixture.

Optional Components

In some embodiments, the aqueous liquid medium may comprise a buffered solution. The ionic conditions of the buffered solution should be such that the enzyme and enzyme substrate are not affected. In some embodiments, a buffer solution is used as part of the aqueous liquid medium, such as phosphate buffers, (e.g., phosphate buffered saline solution, potassium phosphate or potassium phosphate dibasic), tris(hydroxymethyl) aminomethane-HCl solution, or acetate buffer, or any other buffer suitable for sterilization known in the art. Buffers suitable for the present biological indicators should be compatible with fluorogenic and chromogenic enzyme substrates used as part of the aqueous liquid medium. Another consideration in choosing the buffers is their influence on the enzyme activity. For example, phosphate buffered saline contains a relatively high concentration of inorganic phosphate, which is a competitive inhibitor of alkaline phosphatase. Thus, for that enzyme, a Tris-HCl buffer is recommended. The strength of the buffered solution may be from 0.05 M to 0.5 M, preferably from 0.05 M to 0.25 M, more preferably from 0.05 M to 0.15 M, even more preferably about 0.1 M.

In some situations, one or more components of a biological indicator (e.g., crevasses in the housing, pH indicator dye substrates and/or carriers for spores, walls of container, etc.) may retain residual oxidizing sterilant. This can occur, for example, with hydrogen peroxide vapor as well as with other vapor sterilants such as ozone and peracetic acid. For example, certain carrier materials, e.g., those that are hydrophilic such as glass fiber and cellulosic materials, can retain residual oxidizing sterilant, particularly hydrogen peroxide. In this context, "residual" means an amount of retained sterilant that inhibits the growth of low numbers of spore survivors. Typically, this means more than 10 micrograms of sterilant retained per microgram of carrier. In certain situations, the amount of residual sterilant can be greater than 40 micrograms sterilant per milliliter of growth media. As a comparison, if the carrier material has a contact angle of greater than 90°, it is hydrophobic, and there is generally no more than 10 micrograms sterilant retained per microgram of carrier.

Therefore, in some embodiments, the biological indicators comprise one or more neutralizers, which are not an enzyme and not a metal catalyst disposed within the biological indicator. A neutralizer is a compound or material that reacts with residual sterilant, e.g., hydrogen peroxide, to neutralize its effect, wherein the neutralizer is not an enzyme, and not a metal catalyst. Enzyme neutralizers are typically not stable at the high temperatures, and thus not desirable.

Suitable examples of neutralizers include sulfur containing materials such as methionine, L-cysteine, D-ethionine, S-methyl-L-cysteine, S-benzyl-L-cysteine, sodium thiosulfate, glutathionine, L-cystathionine, N-acetyl-L-cysteine, carboxymethylcysteine, D,L-homocysteine, D,L-homocysteine-thiolactone, and thiodipropionic acid, and non-sulfur containing materials such as isoascorbic acid, potassium ferricyanide, and sodium pyruvate. Various combinations of such neutralizers can be used. Preferred neutralizers include methionine, L-cysteine, D-ethionine, S-methyl-L-cysteine, S-benzyl-L-cysteine, sodium thiosulfate, thiodipropionic acid, isoascorbic acid, potassium ferricyanide, sodium pyruvate, and combinations thereof.

pH Indicator Dye

A self-contained biological indicator of the present disclosure comprises a pH indicator dye bound (e.g., with high affinity) to the pH indicator dye substrate material. In any of the embodiments of the method, the indicator dye may be a pH indicator suitable to detect the biological activity. The indicator dye can be selected according to criteria known in the art such as, for example, pH range, compatibility with the biological activity, and solubility. In some embodiments, a salt form of the pH indicator may be used, for example, to increase the solubility of the pH indicator in an aqueous mixture. Nonlimiting examples of suitable pH indicator dyes include, for example, thymol blue, tropeolin OO, methyl yellow, methyl orange, bromophenol blue, bromocresol green, methyl red, bromothymol blue, phenol red, chlorophenol red, neutral red, naphtholphthalein, phenolphthalein, thymolphthalein, alizarin yellow, tropeolin O, nitramine, trinitrobenzoic acid, thymol blue, bromophenol blue, tetrabromphenol blue, bromocresol green, bromocresol purple, methyl red, bromothymol blue, Congo red, and cresol red. In certain embodiments, the pH indicator dye is anionic in a solution having a pH around neutral.

In some embodiments, the pH indicator dye produces a change in color when the pH decreases, indicating growth of the test microorganisms. In some embodiments, the pH indicator dye is bromocresol purple. The pH indicator can be used to detect a biological activity, such as the fermentation of a carbohydrate to acid end products (suggesting survival of the test microorganisms) and an enzymatic biological activity such as α-D-glucosidase enzyme activity, for example. These activities can indicate the presence or absence of a viable spore following the exposure of a biological indicator to a sterilization process, for example. The bromocresol purple can be used at a concentration of about 0.03 g/L in the aqueous mixture, for example.

The combination of bromocresol purple and 4-methylumbelliferyl-α-D-glucoside represents a preferred combination of enzymatic substrate and pH indicator dye in an article or method according to the present disclosure, but other combinations are contemplated within the scope of the present disclosure.

Self-Contained Biological Indicator

The pH indicator dye-bound pH indicator dye substrate described herein can be employed as a modification to a wide variety of biological indicators known in the art to produce a self-contained biological indicator according to the present disclosure. In addition, the pH indicator dye-bound pH indicator dye substrate described herein can be employed as a modification to a wide variety of methods of assessing the effectiveness of a sterilization process.

For example, the self-contained biological indicator of U.S. Pat. No. 3,661,717; which is incorporated herein by reference in its entirety; could be modified to provide the pH-sensitive dye indicator bound to a pH indicator dye substrate as described herein instead of providing it in the aqueous nutrient medium disposed in an inner container (e.g., frangible ampoule). Optionally, a portion of the pH indicator dye substrate could function as the carrier for the test microorganisms (e.g., spores).

In addition, the self-contained biological indicators of U.S. Pat. Nos. 5,223,401 and 6,623,955; which are both incorporated herein by reference in their entirety; could be modified to provide the pH-sensitive dye indicator bound to a pH indicator dye substrate as described herein instead of providing it in the aqueous nutrient medium disposed in an inner container (e.g., frangible ampoule). Optionally, a portion of the pH indicator dye substrate could function as the carrier for the test microorganisms (e.g., spores).

Furthermore, the self-contained biological indicator of U.S. Patent Application Publication No. US 2013/0302849; which is incorporated herein by reference in its entirety; could be modified to provide the pH-sensitive dye indicator bound to a pH indicator dye substrate as described herein instead of providing it in the aqueous nutrient medium disposed in the inner container (e.g., frangible ampoule). For example, the substrate 119 disclosed in U.S. Patent Application Publication No. US 2013/0302849 could be used as the pH indicator dye substrate of a self-contained biological indicator according to the present disclosure.

A person having ordinary skill in the art will recognize how other existing biological indicators could be modified with the pH indicator dye-bound substrate of the present disclosure to arrive at the articles and methods of the present disclosure.

In this disclosure, the process of bringing the spores and medium together is referred to as "activation" of the biological indicator. That is, the term "activation" and variations thereof, when used with respect to a biological indicator refer generally to bringing one or more test microorganisms (e.g., spores) in fluid communication with the aqueous liquid medium (e.g., a liquid medium comprising a nutrient and/or an enzyme substrate). For example, when an openable container within the biological indicator that contains the aqueous liquid medium is at least partially opened (e.g., fractured, punctured, pierced, crushed, cracked, breaking, or the like), such that the medium has been put in fluid communication with the test microorganisms, the biological indicator can be described as having been "activated." Said another way, a biological indicator has been activated when the test microorganisms have been exposed to the aqueous liquid medium that was previously isolated from contact with the test microorganisms.

Method of Assessing the Efficacy of a Sterilization Process

In another aspect the present disclosure provides a method of assessing the efficacy of a sterilization process. In certain implementations, the sterilization process can be a process intended to sterilize an article or a group of articles. In certain implementations, the method is conducted using a sterilizer. In certain implementations, the method is conducted using an automated sterilizer comprising a sterilization chamber and that is programmed to expose an article disposed in the sterilization chamber to a predetermined condition or set of conditions intended to render the article sterile.

The method comprises positioning a biological indicator in a sterilization chamber. The biological indicator comprises: a housing having at least one liquid-impermeable wall that forms an opening into a compartment as disclosed herein, a plurality of test microorganisms disposed in the housing, and a pH indicator dye substrate disposed in the housing.

The pH indicator dye substrate is substantially water-free and has a pH indicator dye bound thereto as disclosed herein. The pH indicator dye is present on the pH indicator dye substrate substantially in a first state (e.g., having a color associated with the pH indicator dye when the dye is predominantly deprotonated). The pH indicator dye can be converted (e.g., by protonation in an aqueous liquid medium) to a second state (e.g., having a color associated with the pH indicator dye when the dye is predominantly protonated) that is optically distinguishable from the first state. When the biological indicator is positioned in the sterilization chamber (i.e., before biological indicator is exposed to the sterilization process), the pH indicator dye is not disposed in, or in liquid contact with, an aqueous liquid medium.

Optionally, in any implementation of the method, the biological indicator further can comprise an aqueous liquid medium disposed in an openable container that is disposed in the housing, as disclosed hereinabove.

Optionally, in any implementation of the method, the biological indicator further can comprise a nutrient composition as described herein that facilitates germination and/or outgrowth of one of the plurality of test microorganisms.

The method further comprises exposing the biological indicator in the sterilization chamber to the sterilization process. The sterilization process can be any sterilization process capable of rendering the test microorganisms non-viable. Nonlimiting examples of sterilization processes include sterilization processes that place the test microorganisms in fluid communication with a sterilant such as steam, ethylene oxide, vapor hydrogen peroxide, ozone, dry heat, ionizing radiation, or combinations thereof.

After the exposing the biological indicator in the sterilization chamber to the sterilization process, the method further comprises contacting in the housing of the biological indicator the test microorganisms and the pH indicator dye with an aqueous liquid medium and a nutrient that facilitates germination and/or growth of the test microorganism. In certain implementations, the nutrient can be disposed in the housing prior to positioning the biological indicator in the sterilization chamber. In certain implementations, the nutrient can be added into the housing (e.g., as a liquid or a dry composition) after exposing the biological indicator in the sterilization chamber to the sterilization process. In certain implementations, the nutrient can be present in the aqueous liquid medium. In certain implementations in which the biological indicator does not comprise a container that contains the aqueous liquid medium, the aqueous liquid medium (e.g., sterile water) can be added into the housing (e.g., via pipette).

In certain implementations, the aqueous liquid medium may be present in (or adjacent) the biological indicator in an openable (e.g., frangible) container. In these implementations, contacting in the housing of the biological indicator the test microorganisms and the pH indicator dye with an aqueous liquid medium comprises opening the openable container (e.g., by crushing a frangible container). In any implementation, the nutrient may be present (e.g., as a dry powder or capsule that dissolves and/or suspends in the aqueous liquid medium, or in an aqueous liquid medium contained in the aforementioned openable container) in the housing of the biological indicator when the biological indicator is positioned in the sterilization chamber. Alternatively, or additionally, the nutrient may be present in an aqueous liquid medium that is added into the housing (e.g., via pipette) after the biological indicator in the sterilization chamber has been exposed to the sterilization process.

After the contacting in the housing of the biological indicator the test microorganisms and the pH indicator dye substrate with an aqueous liquid medium comprising a nutrient, the method further comprises incubating the biological indicator for a period of time. Incubating the biological indicator for a period of time comprises incubating the biological indicator at a specified temperature while the aqueous liquid medium is in contact with the test microorganisms and the pH indicator dye substrate. The specified temperature can be any suitable incubation temperature described herein for the test microorganism and/or the enzyme activity. In certain implementations, the incubation temperature is from about 30° and 40° C. In certain implementations, the incubation temperature is about 52° to 65° C.

The period of time of incubation can be any suitable period of time of incubation suitable to detect an indication of a viable test microorganism in the biological indicator. A change of the pH indicator dye from the first state to the second state is one indication of a viable test microorganism. A presence of a product of an enzyme reaction with a fluorogenic or chromogenic enzyme substrate is another indication of a viable test microorganism. In certain embodiments, the specified period of time is less than 8 hours, in some embodiments, less than 1 hour, in some embodiments, less than 30 minutes, in some embodiments, less than 15 minutes, in some embodiments, less than 5 minutes, and in some embodiments, less than 1 minute. In other embodiments, the suitable incubation time for the biological indicator of this disclosure is from 10 min to 1 hr, or from 10 min to 50 min, or from 10-30 min, or from 10-20 min, or form 10-25 min, or from 15 to 30 min, or from 15-25 min, or from 15-20 min.

After incubating the biological indicator for the period of time, the method further comprises observing the pH indicator dye to detect the second state. The pH indicator dye can be observed visually or by using an automated detector (e.g., a colorimeter). Observing the pH indicator dye to detect the second state comprises observing the pH indicator dye bound to the pH indicator dye substrate. Detecting a presence of the second state of the pH indicator dye on the pH indicator dye substrate indicates a lack of efficacy of the sterilization process. Detecting an absence of the second state of the pH indicator dye on the pH indicator dye substrate indicates efficacy of the sterilization process.

Systems

In another aspect, the present disclosure provides a system that can be used for determining the efficacy of a sterilization process. The system comprises any embodiment of the self-contained biological indicator according to the present invention, and an automated reader. The automated reader is configured to i) receive at least a portion of the biological indicator, ii) direct a first wavelength of electromagnetic radiation into the aqueous liquid medium in the housing, and iii) detect or measure a quantity of a second wavelength of electromagnetic radiation emitted by the fluorescent product. Accordingly, a person having ordinary skill in the art will recognize the automated reader comprises inter alia a locus (e.g., a chamber) dimensioned to receive the biological indicator, a source of ultraviolet electromagnetic radiation, a photodetector for detecting and measuring fluorescence emitted from the biological indicator, at least one microprocessor for controlling components of the automated reader. Optionally, the automated reader further comprises software or firmware comprising an algorithm for identifying biological indicators that exhibit fluorescence indicative of complete inactivation the source of biological activity or survival of at least a portion of the source of biological activity after exposure to a sterilization process.

The present invention is illustrated by the following examples. It is to be understood that the particular examples, materials, amounts, and procedures are to be interpreted broadly in accordance with the scope and spirit of the invention as set forth herein.

EXAMPLES

Example 1. Preparation of pH Indicator-Bound pH Indicator Dye Substrates

The charged-nylon substrate (GE MAGNAPROBE charged nylon) having an area of approximately 1 cm² from 3M™ ATTEST™ 1492V biological indicators were submerged at room temperature in the ampoule medium from 3M ATTEST 1492V biological indicators for one minute, during which substantially all of the bromocresol purple was concentrated out of the medium onto the pH indicator dye substrate. The pH indicator dye substrates were removed from the medium, rinsed with sterile deionized water, and dried at room temperature. The pH indicator dye-bound substrate appeared dark purple. After the pH indicator dye substrates were dry, they were placed onto the housing of the biological indicators as shown for "substrate 119" in FIGS. 1-4 of US Patent Application Publication No. 2013/0302849.

Example 2. Preparation of Biological Indicators

The parts used for this Example were from 3M ATTEST 1492V biological indicators (described in US Patent Application Publication No. 2013/0302849 and obtained from 3M Company, St. Paul, MN). In contrast to the commercially-available 1492V biological indicators, the frangible ampoules containing the nutrient medium and the pH indicator were removed from the biological indicators used in this Example. The pH indicator-bound pH indicator dye substrate was prepared as described in Example 1 and was inserted into the biological indicators (lacking the ampoules of nutrient medium) at the location shown by substrate 119 of US Patent Application Publication No. 2013/0302849.

These biological indicators were used to assess the efficacy of a steam sterilization process as described below.

Although the biological indicators of this Example did not include therein a nutrient that facilitates germination and/or outgrowth of the test microorganisms or an openable container containing an aqueous liquid medium, the inventors recognize that both of these components could be added to the biological indicators of Example 2 to produce self-contained biological indicators.

Example 3. Assessment of the Efficacy of a Sterilization Process

Biological indicators produced as described in Example 2 were placed in a sterilization chamber of an automated steam sterilizer and were exposed to steam at 121° C. for 15 minutes in an AMSCO® Lab 110 steam sterilizer STERIS, Mentor, OH). Control biological indicators from Example 2 were not exposed to a steam sterilization process. After the indicators were removed from the sterilizer, approximately 0.5 mL of a nutrient medium (containing a fermentable carbohydrate) for growing Geobacillus stearothermophilus was pipetted into the steam-exposed biological indicators and the control biological indicators and all of the biological indicators were incubated at 60° C. to permit growth of the spores. After incubation, the pH indicator-bound pH indicator dye substrates in the biological indicators exposed to the steam sterilization process remained dark purple. In contrast, the pH indicator-bound pH indicator dye substrates in the biological indicators that were not exposed to the steam sterilization process appeared yellow.

Reference Example 1

Concentrating pH Indicator Dye Onto pH Indicator Dye Substrate

A charged nylon substrate from a 3M™ ATTEST™ 1492V biological indicator was placed into a cuvette along with approximately 0.5 mL of nutrient medium from the ampoules of 3M™ ATTEST™ 1492V biological indicators. The cuvette with the medium and the substrate was incubated at 58° C. At the time intervals (beginning after contacting the substrate with the medium) shown in Table 1, the absorbance (450 nm) of the nutrient medium was measured using a Thermo Scientific™ GENESYS™ 20 spectrophotometer (Fisher Scientific, Waltham, MA).

The data in Table 1 show that less than half of the pH indicator dye was removed from the nutrient medium during the first 25 minutes of contact between the substrate and the nutrient medium. This indicates that attempting to detect a fluorescent enzyme product in the nutrient medium may be hindered by the remaining pH indicator dye remaining in the medium. In contrast, when the pH indicator dye is bound to a pH indicator dye substrate, there would be little or no interference by the pH indicator dye in detecting a weak fluorescent signal in the nutrient medium.

TABLE 1

| Time course of the removal (at 58° C.) of bromocresol purple pH indicator dye from a nutrient medium by a charged nylon substrate placed into the medium. | |
| --- | --- |
| Time (min) | $A_{450}$ |
| 0.5 | 0.465 ± 0.007 |
| 5 | 0.429 ± 0.003 |

TABLE 1-continued

Time course of the removal (at 58° C.) of bromocresol
purple pH indicator dye from a nutrient medium by
a charged nylon substrate placed into the medium.

| Time (min) | $A_{450}$ |
| --- | --- |
| 19 | 0.402 ± 0.010 |
| 15 | 0.387 ± 0.015 |
| 20 | 0.359 ± 0.016 |
| 25 | 0.345 ± 0.007 |

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The complete disclosures of all patents, patent applications, publications, and nucleic acid and protein database entries which are cited herein, are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A self-contained sterilization process biological indicator, comprising:
    a housing having at least one liquid-impermeable wall that forms an opening into a compartment;
    a plurality of test microorganisms disposed in the housing;
    an aqueous liquid medium disposed in an openable container that is disposed in the housing;
    a nutrient that facilitates germination and/or outgrowth of the test microorganisms;
        wherein the nutrient is disposed in the housing or is disposed in the container;
    a pH indicator dye substrate disposed in the housing, the pH indicator dye substrate having a pH indicator dye bound thereto, wherein the pH indicator is not disposed in or in liquid contact with the aqueous liquid medium; and
    a fluorogenic enzyme substrate or a chromogenic enzyme substrate disposed in the housing.

2. The self-contained sterilization process biological indicator of claim 1, wherein the pH indicator dye substrate is substantially water-free.

3. The self-contained sterilization process biological indicator of claim 1, wherein the pH indicator dye is substantially water-free.

4. The self-contained sterilization process biological indicator of claim 1, wherein the pH indicator dye substrate comprises a cationic polymer.

5. The self-contained sterilization process biological indicator of claim 4, wherein the cationic polymer comprises a polyamide polymer or a polyethyleneimine polymer, a polyvinylidene fluoride polymer, or a combination of any two or more of the foregoing cationic polymers.

6. The self-contained sterilization process biological indicator of claim 1, wherein pH indicator dye is anionically charged in a solvent having a neutral pH.

7. The self-contained sterilization process biological indicator of claim 1, wherein the pH indicator dye is selected from the group consisting of thymol blue, tropeolin OO, methyl yellow, methyl orange, bromophenol blue, bromocresol green, methyl red, bromothymol blue, phenol red, chlorophenol red, neutral red, naphtholphthalein, phenolphthalein, thymolphthalein, alizarin yellow, tropeolin O, nitramine, trinitrobenzoic acid, thymol blue, bromophenol blue, tetrabromphenol blue, bromocresol green, bromocresol purple, methyl red, bromothymol blue, Congo red, and cresol red.

8. The self-contained sterilization process biological indicator of claim 1, wherein the plurality of test microorganisms is disposed on a carrier.

9. The self-contained sterilization process biological indicator of claim 8, wherein the pH indicator dye substrate is the carrier.

10. The self-contained sterilization process biological indicator of claim 1, wherein the test microorganism is a microorganism selected from the group consisting of Geobacillus stearothermophilus, Bacillus stearothermophilus, Bacillus subtilis, Bacillus atrophaeus, Bacillus megaterium, Bacillus coagulans, Clostridium sporogenes, Bacillus pumilus, and a combination of any two or more of the foregoing microorganisms.

11. The self-contained sterilization process biological indicator of claim 1, wherein the aqueous liquid medium comprises the nutrient that facilitates germination and/or growth of the test microorganism.

12. The self-contained sterilization process biological indicator of claim 1, wherein the fluorogenic enzyme substrate or chromogenic enzyme substrate is disposed in the openable container.

13. A method of assessing the efficacy of a sterilization process, the method comprising:
    positioning a self-contained biological indicator in a sterilization chamber, wherein the self-contained biological indicator comprises:
        a housing having at least one liquid-impermeable wall that forms an opening into a compartment;
        a plurality of test microorganisms disposed in the compartment;
        a substantially water-free pH indicator dye substrate disposed in the compartment, the pH indicator dye substrate having a substantially water-free pH indicator dye bound thereto; and
        a fluorogenic enzyme substrate or a chromogenic enzyme substrate disposed in the housing
            wherein the pH indicator dye is present on the pH indicator dye substrate substantially in a first state and wherein the pH indicator dye can be converted to a second state that is optically distinguishable from the first state;
    exposing the biological indicator in the sterilization chamber to the sterilization process;
    contacting, in the housing of the biological indicator the test microorganisms and the pH indicator dye substrate with an aqueous liquid medium and a nutrient that facilitates germination and/or growth of the test microorganism;
    incubating the biological indicator for a period of time; and
    determining whether the pH indicator dye is in the first state or the second state, wherein the pH indicator dye in the second state indicates a lack of efficacy of the sterilization process.

14. The method of claim 13, wherein the biological indicator further comprises an aqueous liquid medium disposed in an openable container that is disposed in the housing, wherein contacting in the housing of the biological indicator the test microorganisms and the pH indicator dye substrate with the aqueous liquid medium comprises opening the openable container.

\* \* \* \* \*